(12) United States Patent
Bruszewski et al.

(10) Patent No.: US 7,963,960 B2
(45) Date of Patent: Jun. 21, 2011

(54) CUTTING RADIO FREQUENCY CATHETER FOR CREATING FENESTRATIONS IN GRAFT CLOTH

(75) Inventors: Walter Bruszewski, Guerneville, CA (US); Patrick Macaulay, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 806 days.

(21) Appl. No.: 11/557,204

(22) Filed: Nov. 7, 2006

(65) Prior Publication Data

US 2008/0108987 A1    May 8, 2008

(51) Int. Cl.
*A61B 18/14* (2006.01)

(52) U.S. Cl. .......... 606/32; 606/41; 606/45; 606/46

(58) Field of Classification Search ............ 606/32, 606/41, 45
See application file for complete search history.

(56) References Cited

U.S. PATENT DOCUMENTS

| 4,682,596 | A | * | 7/1987 | Bales et al. ............... 606/39 |
| 5,098,431 | A |   | 3/1992 | Rydell |
| 5,507,743 | A | * | 4/1996 | Edwards et al. ............ 606/41 |
| 5,562,720 | A | * | 10/1996 | Stern et al. ............... 607/98 |
| 5,687,723 | A | * | 11/1997 | Avitall ................... 600/374 |
| 5,807,249 | A | * | 9/1998 | Qin et al. ................. 600/374 |
| 6,071,281 | A | * | 6/2000 | Burnside et al. ............ 606/41 |
| 6,149,681 | A |   | 11/2000 | Houser et al. |
| 7,662,150 | B2 | * | 2/2010 | White .................... 606/41 |
| 2002/0004631 | A1 | * | 1/2002 | Jenkins et al. ............ 600/374 |
| 2002/0087208 | A1 | * | 7/2002 | Koblish et al. ............ 607/113 |
| 2004/0181253 | A1 |   | 9/2004 | Sepetka et al. |
| 2005/0209673 | A1 |   | 9/2005 | Shaked |
| 2005/0222668 | A1 |   | 10/2005 | Schaeffer et al. |
| 2006/0106375 | A1 | * | 5/2006 | Werneth et al. ............ 606/32 |
| 2006/0247613 | A1 | * | 11/2006 | White .................... 606/41 |
| 2007/0118099 | A1 |   | 5/2007 | Trout |
| 2007/0168018 | A1 |   | 7/2007 | Amplatz et al. |

FOREIGN PATENT DOCUMENTS

| EP | 0834287 | 4/1998 |
| GB | 2437058 | 10/2007 |
| WO | WO2006/031541 | 3/2006 |
| WO | WO2007/028112 | 3/2007 |

* cited by examiner

*Primary Examiner* — Linda C Dvorak
*Assistant Examiner* — Amanda Scott (57) ABSTRACT

RF power is applied to a circular RF electrode cutting a side opening in a graft material of a main stent-graft in situ. As the side opening is formed by the applied RF power and the associated plasma discharge, the side opening is formed with a minimal application of force to the graft material. Further, the side opening is circular and has a fused edge.

18 Claims, 10 Drawing Sheets

CUTTING RADIO FREQUENCY CATHETER FOR CREATING FENESTRATIONS IN GRAFT CLOTH

BACKGROUND OF THE INVENTION

1. Field of the Invention

The present invention relates to an intra-vascular device and method. More particularly, the present invention relates to a device for treatment of intra-vascular diseases.

2. Description of Related Art

A conventional main (vessel) stent-graft typically includes a radially expandable reinforcement structure, formed from a plurality of annular stent rings, and a cylindrically shaped layer of graft material, sometimes called graft cloth, defining a lumen to which the stent rings are coupled. Main stent-grafts are well known for use in tubular shaped human vessels.

To illustrate, endovascular aneurysmal exclusion is a method of using a main stent-graft to exclude pressurized fluid flow from the interior of an aneurysm, thereby reducing the risk of rupture of the aneurysm and the associated invasive surgical intervention.

Main stent-grafts with custom side openings are sometimes fabricated to accommodate the particular vessel structure of each individual patient. Specifically, as the location of branch vessels emanating from a main vessel, e.g., having the aneurysm, varies from patient to patient, main stent-grafts are fabricated with side openings customized to match the position of the branch vessels of the particular patient. However, custom fabrication of main stent-grafts is relatively expensive and time consuming.

To avoid custom fabrication of main stent-grafts, side openings in the main stent-graft may be formed in situ. Illustratively, the main stent-graft is placed in the main vessel, e.g., the aorta, to exclude an aneurysm. Fenestrations may be made in situ to correspond to adjacent branches.

The graft material of the main stent-graft is pierced with a needle at the ostium of a branch vessel, e.g., the renal artery, emanating from the main vessel. An expandable balloon is then inserted in the needle perforation in the graft material of the main stent-graft.

A fenestration is typically initiated with a small needle perforation of the graft cloth. The perforation must be enlarged with a conical dilator However, considerable force is required to expand the balloon and tear the graft material. The application of such a considerable force is difficult to control thus leads to unpredictability in the tear of the graft material or other complications. Further, the branch stent-graft tends to propagate the rent (a split or tear) in the graft material over time. Further, the edge of the rent fractured the branch stent-graft depending upon the particular application. Finally, the edge of the rent was a fray of loose fibers of the graft material, which tended to unwind over time.

SUMMARY OF THE INVENTION

In accordance with one example, RF power is applied to a circular RF electrode cutting a side opening in a graft material of a main stent-graft in situ. As the side opening is formed by the applied RF power and the associated plasma discharge, the side opening is formed with a minimal application of force to the graft material.

The side opening is defined by a side opening edge of the graft material. The side opening edge is circular. Accordingly, the side opening edge resists tearing of the graft material at the side opening compared to a rent where tearing force is concentrated at the graft material at the ends of the rent.

Further, the side opening edge is fused, i.e., the graft material is melted together at the side opening edge, as compared to the frayed edges of a rent or cut. Accordingly, tattering of the side opening edge is avoided. Further, the fused and circular side opening edge applies even pressure to a branch stent-graft inserted in the side opening thus avoiding damage or destruction to the branch stent-graft.

Embodiments are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

Figure 6:
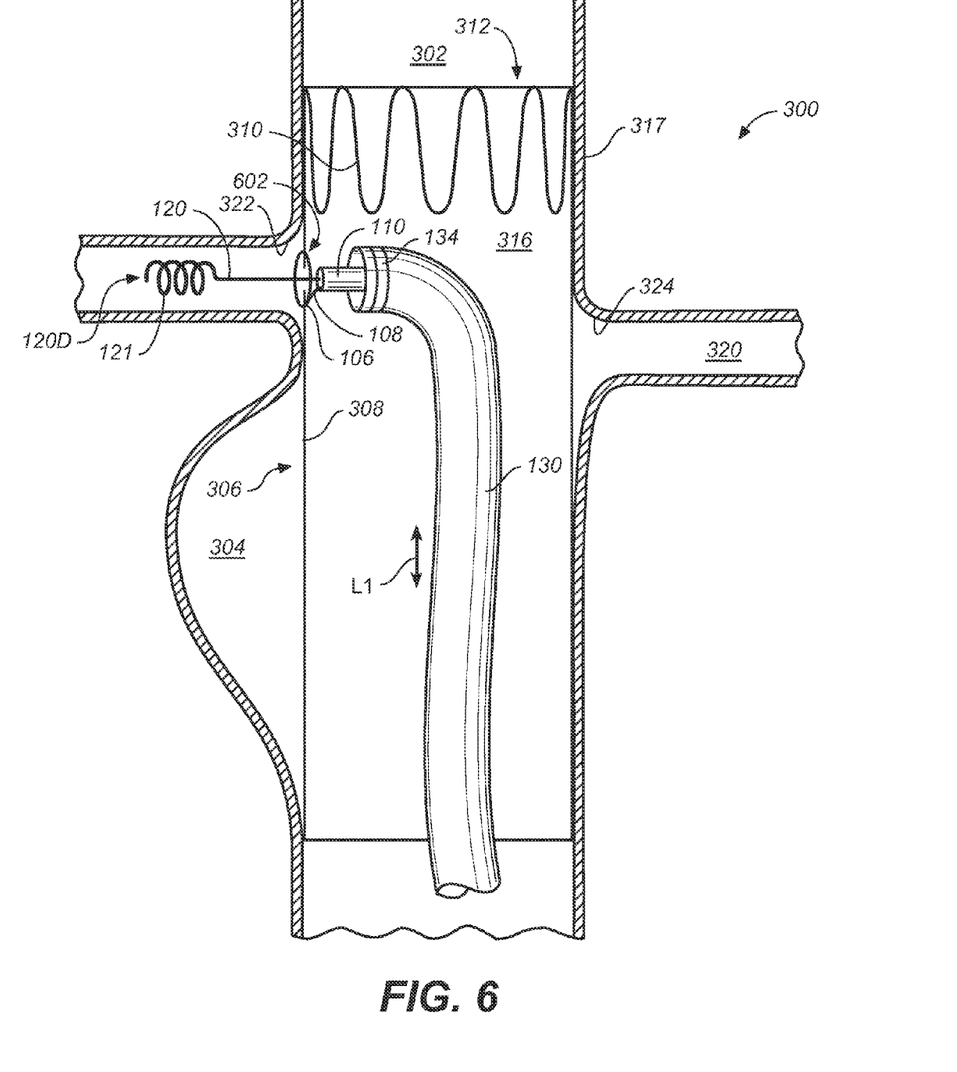

In accordance with one example, referring to FIG. 6, RF power is applied to a circular RF electrode 106 creating a localized knife which is useful in cutting a side opening 602 in a graft material 308 of a main stent-graft 306 in situ. As side opening 602 is formed by the applied RF power and the associated plasma discharge, side opening 602 is formed with a minimal application of force to graft material 308.

Figure 7:
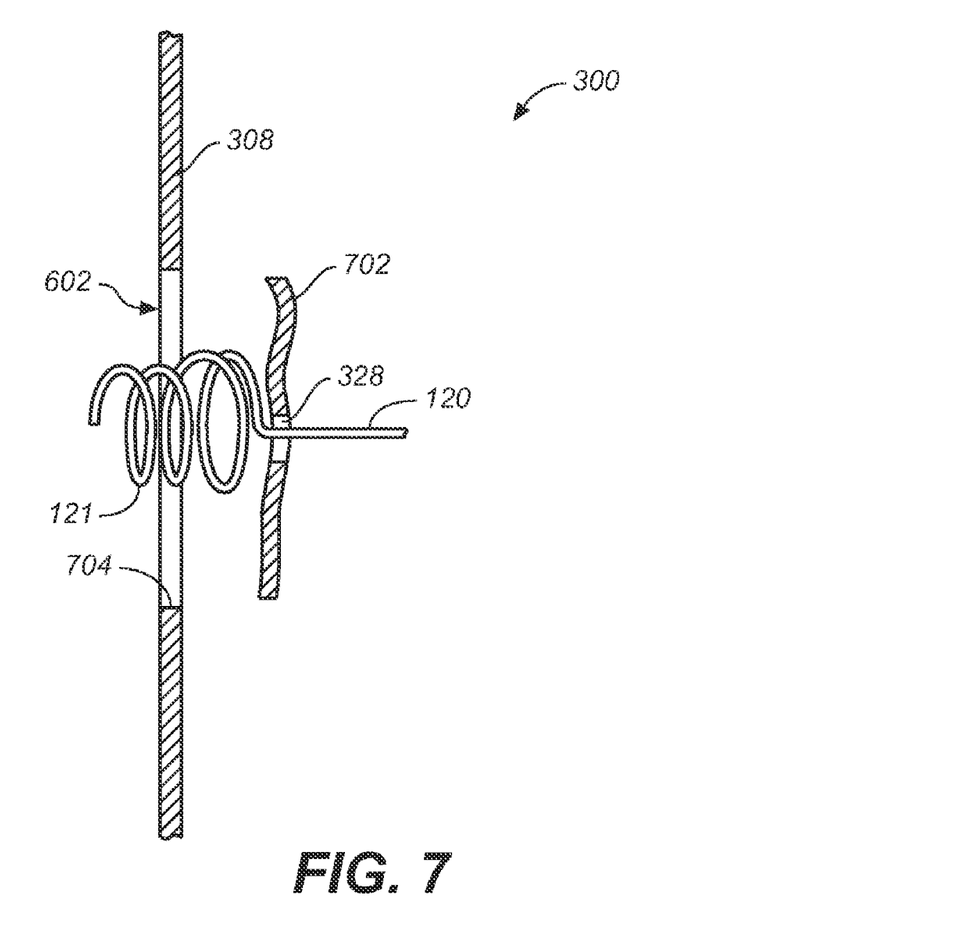
FIG. 7 is an enlarged cross-sectional view of the vessel assembly of FIG. 6 including the side opening formed in the graft material.

Referring now to FIG. 7, a side opening edge 704 defines side opening 602 in graft material 308. In one example, side opening edge 704 is circular in shape, i.e., is a circle. Accordingly, side opening edge 704 resists tearing of graft material 308 at side opening 602 compared to a rent where tearing force is concentrated at the graft material at the ends of the rent.

Further, side opening edge 704 is fused, i.e., the fibers, sometimes called yarn, of graft material 308 are melted together at side opening edge 704, as compared to the frayed edges of a rent or cut. Accordingly, tattering of side opening edge 704 is avoided. Further, the fused and circular side opening edge 704 applies even pressure to a branch stent-graft inserted in side opening 602 thus avoiding damage or destruction to the branch stent-graft.

Figure 1:
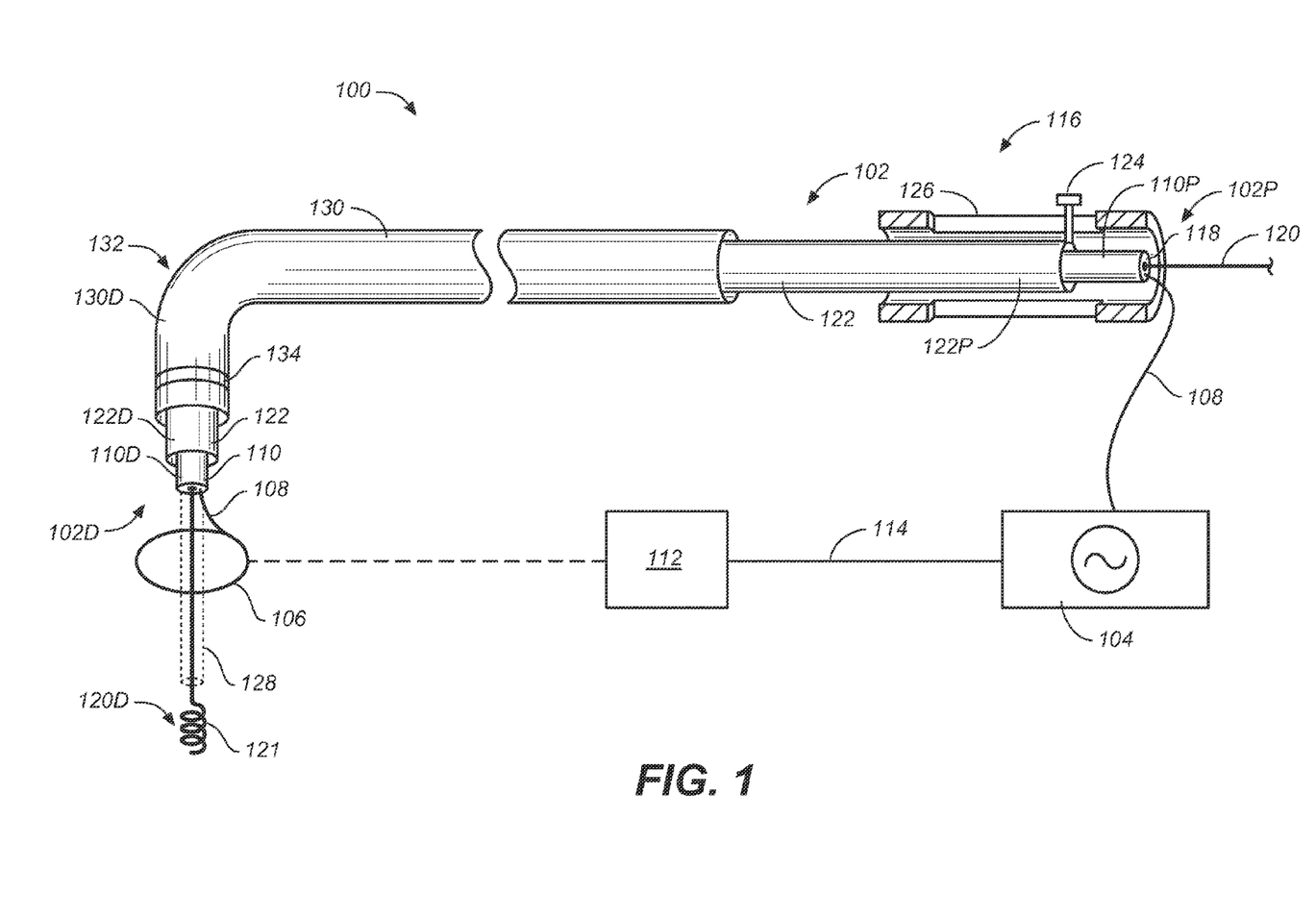
FIG. 1 is a perspective view, partially in cross-section, of a cutting radio frequency (RF) catheter assembly in accordance with one example.

More particularly, FIG. 1 is a perspective view, partially in cross-section, of a cutting radio frequency (RF) catheter assembly 100 including an RF catheter 102 and an RF power supply 104 in accordance with one example. RF catheter 102 includes a proximal end 102P and a distal end 102D. As used herein, proximal end 102P of RF catheter 102 is referenced with respect to the operator's handle, i.e., handle 116.

Figure 2:
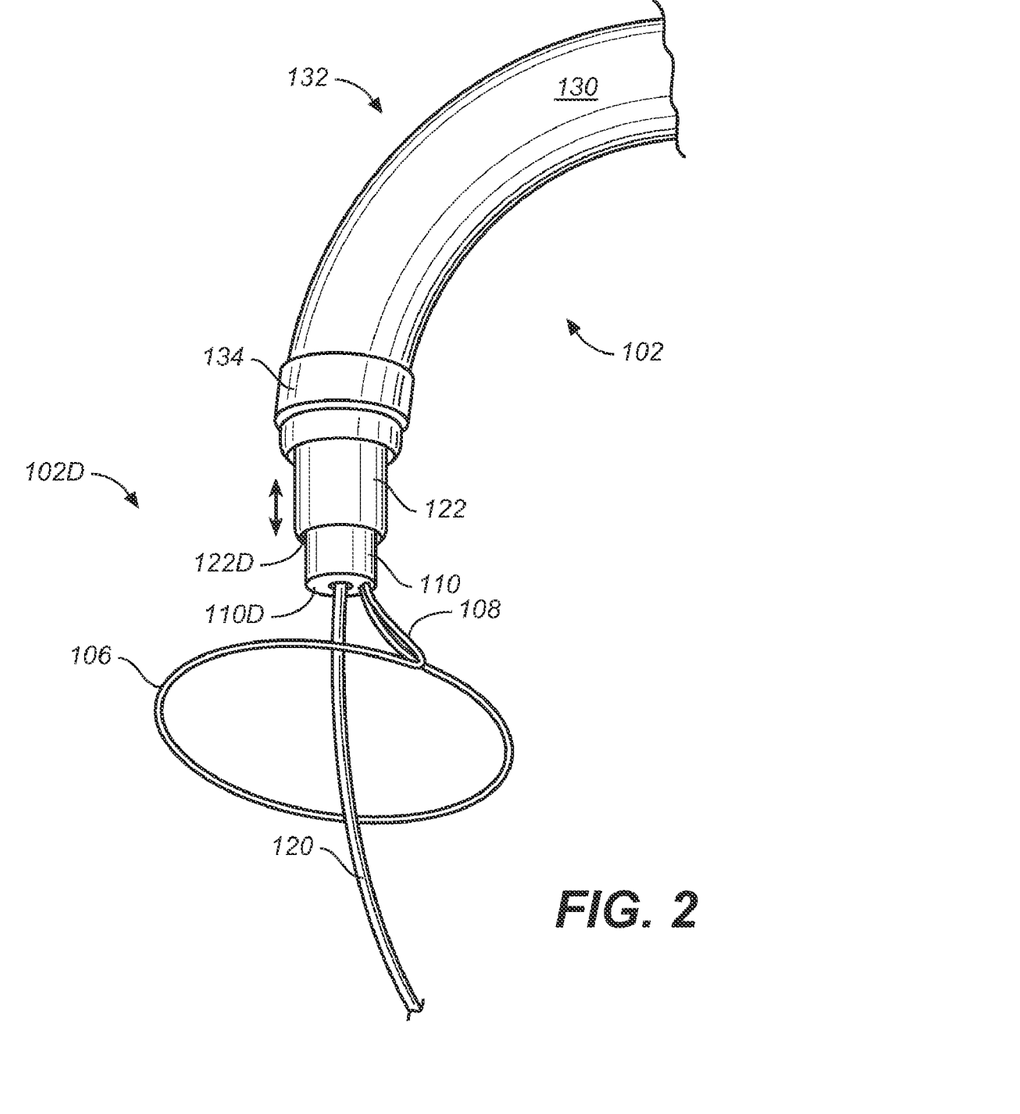
FIG. 2 is an enlarged perspective view of a distal end including an RF electrode of the RF catheter of FIG. 1.

FIG. 2 is an enlarged perspective view of distal end 102D including an RF electrode 106 of RF catheter 102 of FIG. 1.

Referring now to FIGS. 1 and 2 together, RF electrode 106 is in the shape of a closed circle, i.e., is circular, sometimes called a continuous hoop, a continuous loop, or an unbroken circle. In various examples, the diameter of RF electrode 106 is in the range of 5 mm to 7 mm, e.g., is 7 mm. Generally, RF electrode 106 is formed of an electrically conductive material.

In one example, RF electrode 106 is formed of a super elastic memory material, e.g., nitinol, shape set into a circular loop. In other examples, RF electrode 106 is formed of a radiopaque material to aid in visualization of RF electrode 106 using an imaging process, for example, so that RF electrode 106 is visible using x-rays. Illustrative examples of radiopaque materials of which RF electrode 106 is formed include platinum-iridium, tantalum, and/or gold.

RF electrode 106 is supported by and electrically connected to an RF conductor 108. Illustratively, RF conductor 108 is formed of the same material as RF electrode 106. In one specific example, RF electrode 106 and RF conductor 108 are integral, i.e., are a single piece and not a plurality of separate pieces connected together. In another example, RF conductor 108 is attached to RF electrode 106, e.g., by welding. Further, to avoid plasma generation from RF conductor 108, in one embodiment, RF conductor 108 includes a dielectric coating, e.g., RF conductor 108 is electrically conductive metal covered with a dielectric material such as a silicone elastomer.

RF conductor 108 extends proximally from RF electrode 106 and into a distal end 110D of an inner member 110, sometimes called a cutting catheter shaft. RF conductor 108 extends through the length of inner member 110 and exits at a proximal end 110P of inner member 110.

RF conductor 108 is electrically connected to RF power supply 104. During use, RF power supply 104 supplies RF power to RF conductor 108 and thus to RF electrode 106. Illustratively, RF power supply 104 operates in the 500 kHz to 2 MHz frequency range. In one example, the frequency at which RF power supply 104 operates is greater than the threshold for excitation of tissue to avoid tissue excitation.

As another example, the power output of RF power supply 104 is in the range of 50 to 200 watts. For example, RF power supply 104 is a Pfizer Valley Lab Cautery RF generator although any one of a number of RF generators can be used. Although particular frequency and power output ranges are provided, these are illustrative only.

RF power supply 104 is also electrically connected to a counter electrode 112, sometimes called the ground or common electrode, by a counter electrode conductor 114. During use, counter electrode 112, e.g., a conductive metal plate (stainless steel), is electrically connected to the patient for example, using an electrically conductive gel. Counter electrode 112 forms the counter electrode for RF electrode 106 thus completing the circuit.

RF catheter 102 further includes a handle 116. Proximal end 110P of inner member 110 is located at a guide wire port 118 of handle 116. Inner member 110 is a hollow tubular member and defines a guide wire lumen therein. A guide wire 120, e.g., a 0.014 inch guidewire, enters the guide wire lumen of inner member 110 at distal end 110D, extends through the length of inner member 110 inside of the guide wire lumen, and exits proximal end 110P of inner member 110 at guide wire port 118. In one example, guide wire 120 includes a dielectric coating or is formed of a dielectric material to prevent electrical coupling of RF power from RF electrode 106 to guide wire 120. In another example, as discussed further below, guide wire 120 is retracted into distal end 110D of inner member 110 prior to coupling RF power to RF electrode 106.

In one example, guide wire 120 includes a catching structure 121 (corkscrew like shaped structure) at a distal end 120D of guide wire 120. Illustratively, guide wire 120 includes a super elastic memory material, e.g., nitinol, at distal end 120D, which takes the shape of catching structure 121. As discussed further below, catching structure 121 catches the flap of graft material cut from the graft material by RF electrode 106. However, in another example, a guide wire similar to guide wire 120 is formed without a catching structure 121.

RF catheter 102 further includes a retractable sheath 122 for delivering RF electrode 106. A proximal end 122P of sheath 122 is located within handle 116. Proximal end 122P is connected to a thumb slider 124, sometimes called an actuation button. Thumb slider 124 extends from proximal end 122P of sheath 122 inside of handle 116 through a longitudinal slit 126 to the outside of handle 116. Thumb slider 124 is retracted and advanced relative to handle 116 thus retracting and advancing (moving) sheath 122 relative to inner member 110. Recall that proximal end 110P of inner member 110 is connected to handle 116 at guide wire port 118 and thus inner member 110 is fixed relative to handle 116.

Sheath 122 is a hollow tubular member and includes an inner member lumen in which inner member 110 is located. As discussed further below, in one example, RF electrode 106 is initially radially constrained inside of sheath 122. Sheath 122 is retracted by retracting thumb slider 124 thus exposing RF electrode 106, which self-expands, e.g., into the shape illustrated in FIG. 1.

After using RF electrode 106 to form a side opening in the graft material of the main stent-graft as discussed below, sheath 122 is advanced by advancing thumb slider 124. During advancement, distal end 122D of sheath 122 collapses and covers RF electrode 106.

In one embodiment, inner member 110 includes a tubular RF electrode extension portion 128 (shown in dotted lines) which extends distally past the point where RF conductor 108 exits inner member 110. Accordingly, RF electrode 106 is collapsed within the annular space between RF electrode extension portion 128 of inner member 110 and sheath 122.

Cutting RF catheter assembly 100 further includes a delivery catheter 130. In one example, delivery catheter 130 is a steerable guiding catheter. It another example, delivery catheter 130 is a pre-curved catheter having a bend 132, e.g., a 90 degree bend, formed at a distal end 130D of delivery catheter 130.

Delivery catheter 130 is a hollow tubular member which defines a lumen. Inner member 110 including RF electrode 106 and sheath 122 are advanced through the lumen of delivery catheter 130. Delivery catheter 130 directs RF electrode 106, e.g., at a 90 degree angle from the length of RF catheter 102.

Delivery catheter 130 includes a radiopaque marker 134 at distal end 130D of delivery catheter 130. Radiopaque marker 134 allows the location of distal end 130D to be visualized using any one of a number imaging techniques. In another example, delivery catheter 130 is not used.

In one example, an RF catheter similar to RF catheter 102 is formed without sheath 122. In accordance with this example, inner member 110 and thus RF electrode 106 are advanced through delivery catheter 130. As RF electrode 106 exits distal end 130D of delivery catheter 130, RF electrode 106 self expands. Further, after use of RF electrode 106 as discussed further below, RF electrode 106 is pulled back into distal end 130D, which collapses and covers RF electrode 106.

Figure 3:
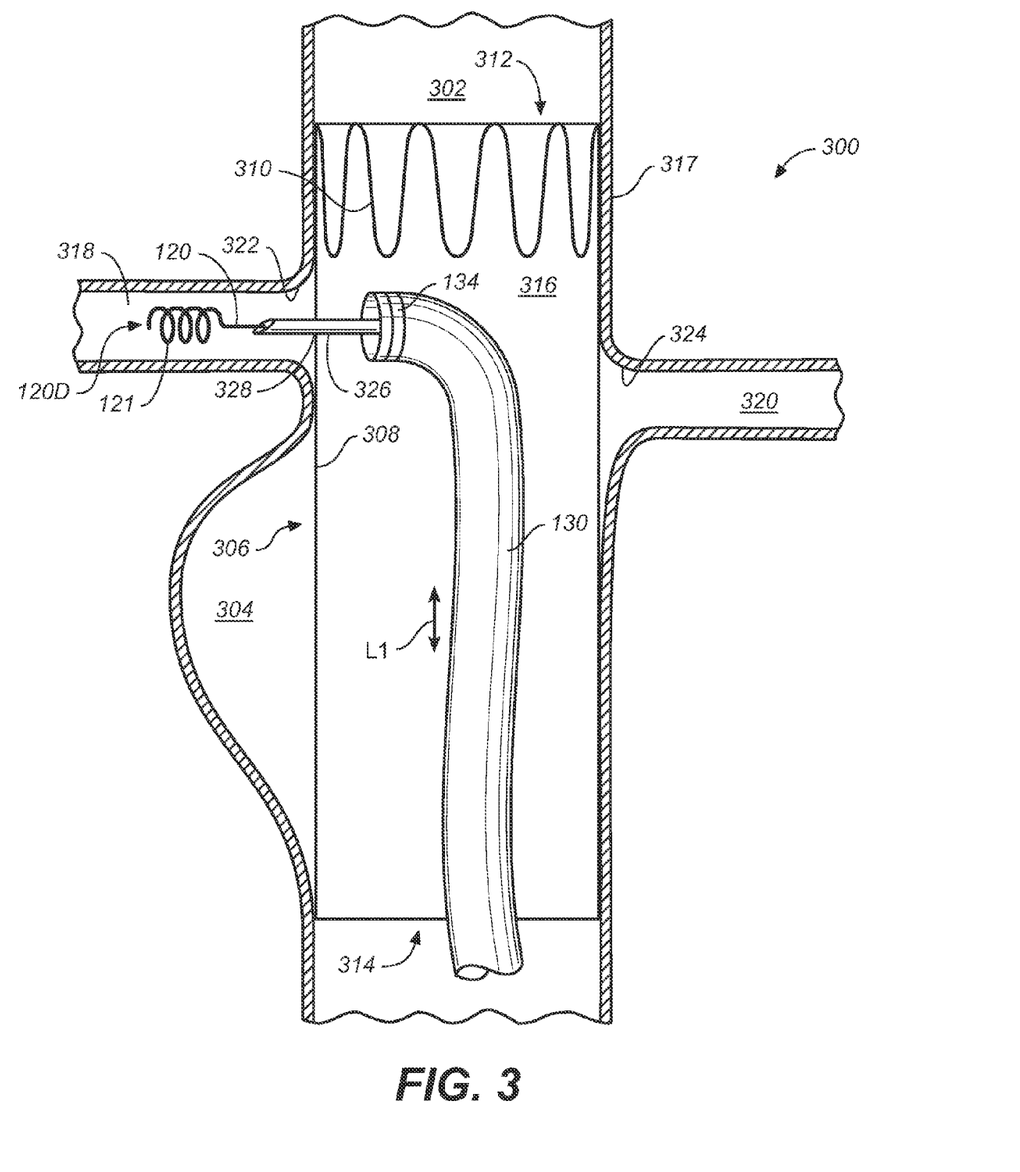
FIG. 3 is a cross-sectional view of a vessel assembly in accordance with one embodiment.

FIG. 3 is a cross-sectional view of a vessel assembly 300 in accordance with one embodiment. Referring now to FIG. 3, a main vessel 302, e.g., the aorta, includes an aneurysm 304. A main stent-graft 306, e.g., an abdominal aortic stent-graft, is deployed into main vessel 302 to exclude aneurysm 304.

In accordance with this example, main stent-graft 306, sometimes called a prosthesis, includes a graft material 308 and a stent ring 310. Graft material 308 is cylindrical having a longitudinal axis L1.

Graft material 308 includes an upper, e.g., first, primary opening 312 and a lower, e.g., second, primary opening 314 at the ends of graft material 308. Graft material 308 defines a lumen 316 longitudinally extending from upper primary opening 312 to lower primary opening 314. During use, fluid, e.g., blood, flows through lumen 316 and more generally through graft material 308 thus excluding aneurysm 304.

Stent ring 310 is connected to main stent-graft 306, for example, with stitching. Stent ring 310 is a radially expandable reinforcement structure that self expands into a vessel wall 317 of main vessel 302 thus anchoring main stent-graft 306 in place. Although only a single stent ring 310 is set forth, in other examples, a main stent-graft similar to main stent-graft 306 is formed with a plurality of stent rings or other radially expandable reinforcement structures.

Emanating from main vessel 302 is a first branch vessel 318 and a second branch vessel 320. The location of branch vessels 318, 320 vary from patient to patient. Thus, side openings corresponding to ostiums 322, 324 of branch vessel 318, 320, respectively, are formed in graft material 308 in situ after main stent-graft 306 is deployed within main vessel 302 as set forth below.

To form a side opening in graft material 308 corresponding to (at) branch vessel 318, e.g., a renal artery (RA) or a superior mesenteric artery (SMA), sometimes called a visceral branch, delivery catheter 130 is advanced to the location of branch vessel 318. Radiopaque marker 134 is used to facilitate this positioning of delivery catheter 130. Distal end 130D is oriented radially, e.g., at a 90 degree angle, relative to longitudinal axis L1 and thus points at graft material 308 and within ostium 322 of branch vessel 318.

A hollow needle 326, e.g., similar to a hypodermic needle, is advanced through the lumen of delivery catheter 130. Needle 326 pierces graft material 308 adjacent ostium 322 thus forming a small, e.g., first, opening 328 in graft material 308. Small opening 328 is sometimes called a central opening.

Guide wire 120 is advanced through the lumen of needle 326 through graft material 308 and deployed into branch vessel 318. In accordance with this example, as guide wire 120 exits needle 326, guide wire 120 forms catching structure 121 at distal end 120D of guide wire 120. Illustratively, catching structure 121 is formed of a super elastic memory material, e.g., nitinol, and thus assumes the shape of catching structure 121 as guide wire 120 is fed out of needle 326.

Generally, the lateral span of the catching structure 121 is larger in diameter than small opening 328. As discussed further below, guide wire 120 including catching structure 121 are used to catch the flap cut from graft material 308 and remove the flap from the patient.

Catching structure 121 is shown as a helix but can be formed in any one of a number of shapes.

Needle 326 is retracted leaving guide wire 120 extending through small opening 328.

Figure 4:
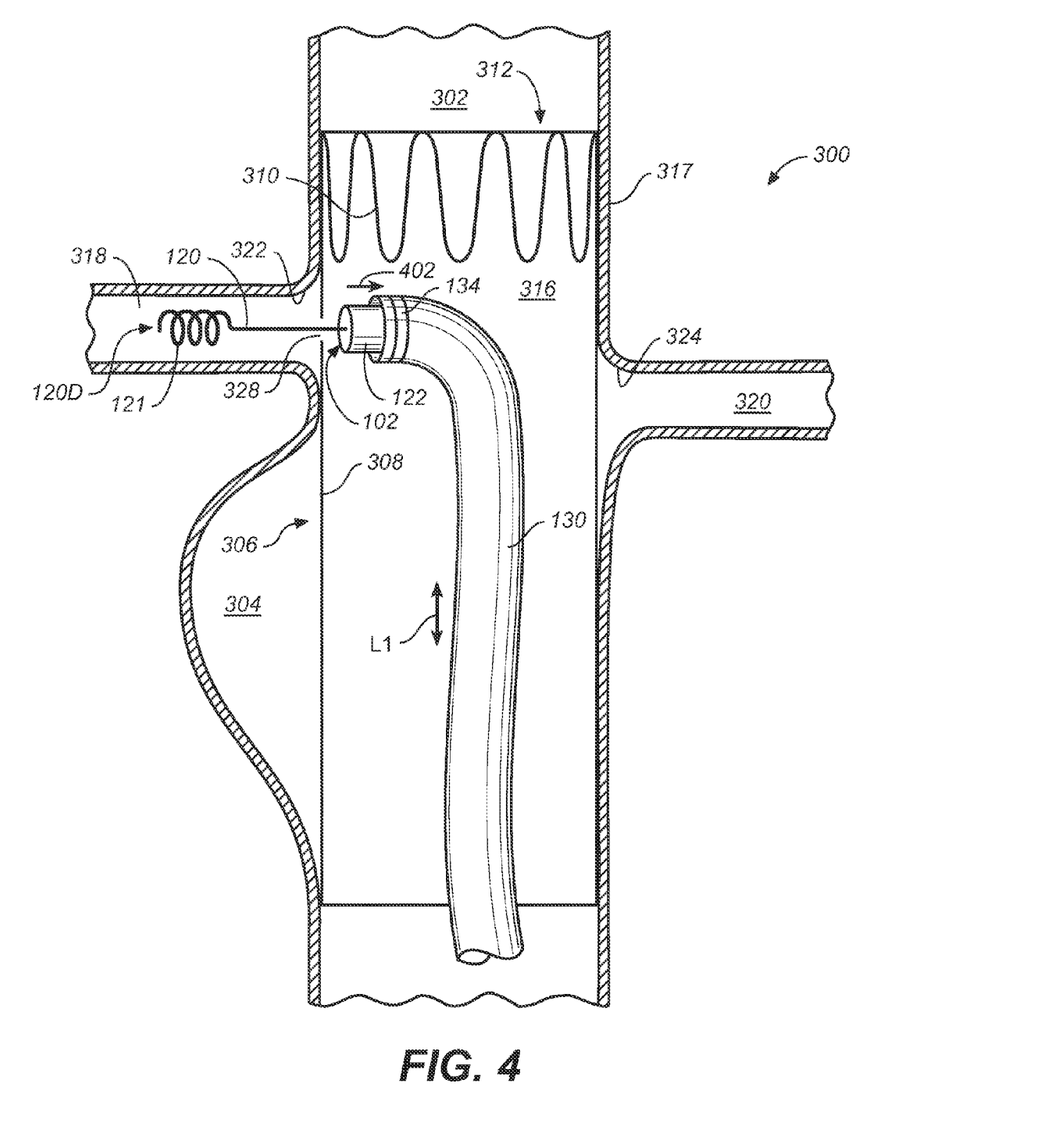
FIGS. 4, 5, and 6 are cross-sectional views of the vessel assembly of FIG. 3 at further stages during formation of a side opening in a graft material.
Figure 5:
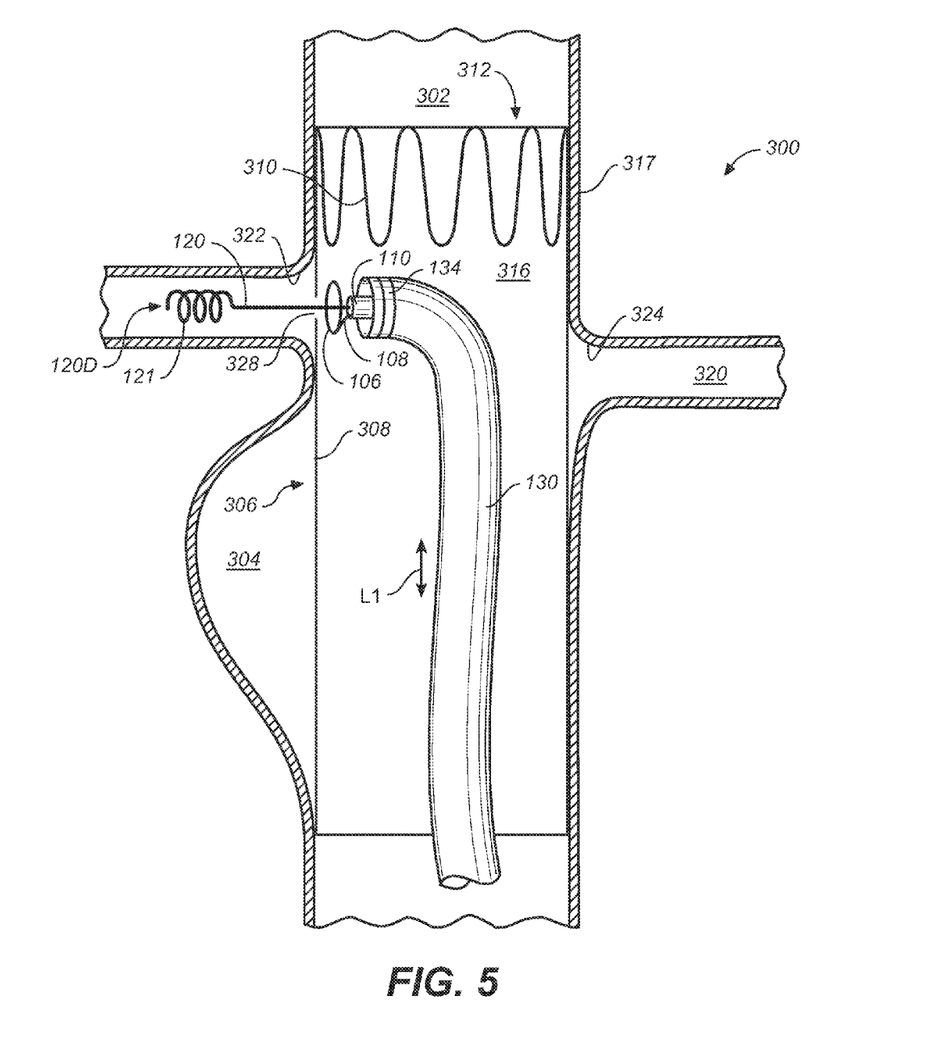

FIGS. 4 and 5 are cross-sectional views of vessel assembly 300 of FIG. 3 at further stages during formation of a side opening in graft material 308. Referring now to FIGS. 4 and 5 together, RF catheter 102 is advanced over the guidewire 120 through the lumen of delivery catheter 130 to graft material 308 adjacent (opposite) ostium 322 of branch vessel 318.

As indicated by arrow 402 in FIG. 4, sheath 122 is retracted thus uncovering RF (loop) electrode 106. Upon being uncovered, RF electrode 106 self expands into an expanded circular shape as shown in FIG. 5.

FIG. 6 is a cross-sectional view of vessel assembly 300 at a further stage during formation of a side opening in graft material 308. As shown in FIG. 6, RF electrode 106 is advanced to be adjacent to or in contact with graft material 308 at ostium 322 of branch vessel 318. RF power is applied to RF electrode 106 thus cutting graft material 308 in a shape corresponding to RF electrode 106 and forming a side opening 602 in graft material 308. In various examples, side opening 602 is a 5 mm or 7 mm circular opening.

It is believed that upon application of RF power to RF electrode 106, the fluid, e.g., blood, surrounding RF electrode 106 becomes heated until an electrical plasma is generated. This plasma, sometimes called a plasma discharge, vaporizes the graft material 308 directly adjacent RF electrode 106. Although one theory of operation is set forth, this example is not limited to this particular theory, and other modes of operation are possible. For example, an arc between RF electrode 106 and graft material 308 cuts graft material 308. In another example, RF electrode 106 itself becomes heated by the RF power and thus thermally cuts graft material 308.

In one example, upon application of RF power to RF electrode 106, side opening 602 is formed in graft material 308. It accordance with this example, RF electrode 106 is held stationery and thus side opening 602 is formed without application of force to graft material 308.

In another example, upon application of RF power to RF electrode 106, RF electrode 106 is advanced to pass through graft material 308 slightly. However, as the cutting of graft material 308 is performed by the RF power coupled to RF electrode 106, side opening 602 is formed with a minimal application of force to graft material 308. Further, as discussed further below in reference to FIG. 7, the side opening edge of side opening 602 is fused graft material 308, i.e., has an absence of loose dangling fibers of graft material 308.

FIG. 7 is an enlarged cross-sectional view of vessel assembly 300 of FIG. 6 including side opening 602 formed in graft material 308. Referring now to FIGS. 6 and 7 together, after coupling of RF power to RF electrode 106 and formation of side opening 602, RF electrode 106 is withdrawn from the patient. Illustratively, sheath 122 (FIG. 4) is advanced thus collapsing and covering RF electrode 106. RF catheter 102 is then retracted from delivery catheter 130.

As shown in FIG. 7, an annular shaped flap 702 cut from graft material 308 is held by guide wire 120. Further, catching structure 121 of guide wire 120 is larger in diameter than small opening 328 in flap 702 preventing flap 702 from sliding off of guide wire 120. Guide wire 120 including flap 702 are then withdrawn from the patient.

As also shown in FIG. 7, graft material 308 now includes a side opening edge 704 formed when RF electrode 106 cut side opening 602 in graft material 308. More particularly, side opening edge 704 defines side opening 602 in graft material 308.

In one example, side opening edge 704 is circular in shape, i.e., is a circle. Accordingly, side opening edge 704 resists tearing of graft material 308 at side opening 602 compared to a rent where tearing force is concentrated at the graft material at the ends of the rent.

Further, side opening edge 704 is fused, i.e., the fibers, sometimes called yarn, of graft material 308 are melted together at side opening edge 704 as compared to the frayed edges of a rent or cut. Accordingly, tattering of side opening edge 704 is avoided. Further, the fused and circular side opening edge 704 applies even pressure to a branch stent-graft such as that illustrated in FIG. 8 inserted in side opening 602 thus avoiding damage or destruction to the branch stent-graft.

Figure 8:
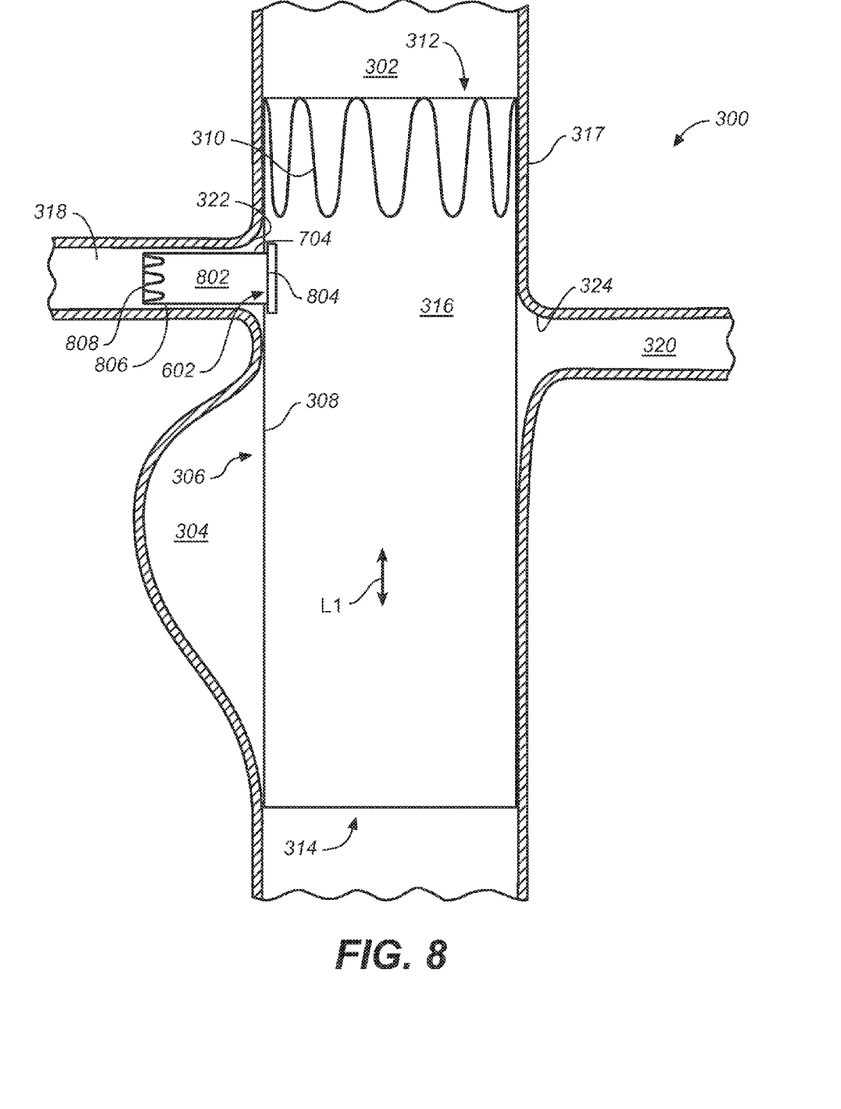
FIG. 8 is a cross-sectional view of the vessel assembly of FIG. 6 at a later stage of assembly illustrating the deployment of a branch stent-graft into the side opening in the graft material.

FIG. 8 is a cross-sectional view of vessel assembly 300 of FIG. 6 at a later stage of assembly illustrating the deployment of a branch stent-graft 802 into side opening 602 in graft material 308. As shown in FIG. 8, branch stent-graft 802 is inserted into side opening 602 and extends into branch vessel 318. Illustratively, branch stent-graft 802 is radially constrained within a sheath (not shown) and positioned inside of side opening 602 and branch vessel 318. The sheath is retracted, uncovering branch stent-graft 802, which self expands into position. However, branch stent-graft 802 can be deployed using other techniques.

In one example, branch stent-graft 802 includes a flange 804 or other locking structure to lock branch stent-graft 802 to main stent-graft 306. In another example, branch stent-graft 802 self expands into side opening edge 704 to lock branch stent-graft to main stent-graft 306. The fused and circular side opening edge 704 applies even pressure to branch stent-graft 802 thus avoiding damage or destruction to branch stent-graft 802.

Branch vessel graft material 806 of branch stent-graft 802 extends from side opening 602 and into branch vessel 318. A stent ring 808 anchors the end of branch vessel graft material 806 in branch vessel 318 and generally maintains patency of branch vessel 318. During use, fluid flows from lumen 316 of main stent-graft 306 through the lumen of branch stent-graft 802 and into branch vessel 318. In one example, the above operations are performed to form a side opening corresponding to second branch vessel 320 and a second branch stent-graft is inserted therein to perfuse second branch vessel 320.

Although a particular sequence of operations are set forth above, in other examples, other sequences of operations are performed. For example, referring to FIG. 6, guide wire 120 (absent catching structure 121 in accordance with this example) is retracted prior to the application of RF power to RF electrode 106. In another example, delivery catheter 130 is not used.

In another example, guide wire 120 is deployed after side opening 602 is formed. Branch stent-graft 802 is advanced over guide wire 120 in accordance with this example.

In another example, referring to FIG. 3, small opening 328 is not formed. In accordance with this example, referring now to FIG. 6, side opening 602 is formed in a single operation by application of RF power to RF electrode 106.

Figure 9:
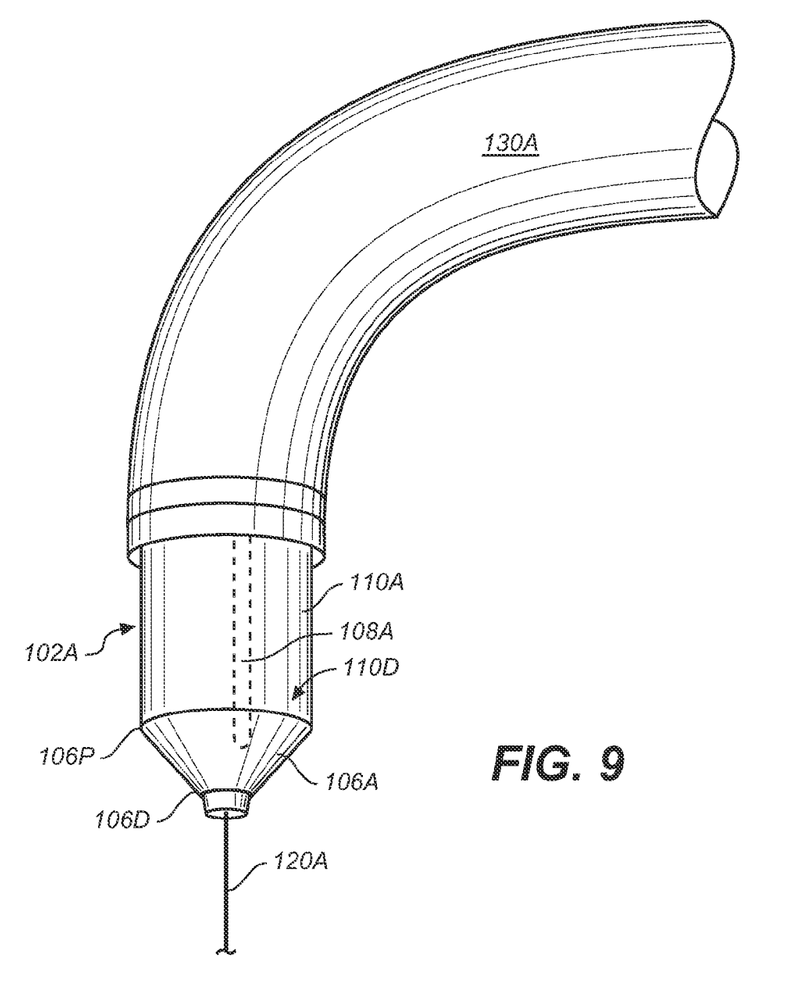
FIG. 9 is a perspective view of an RF catheter having an RF electrode in accordance with another embodiment.

In another example, referring to FIG. 3, to avoid the application of force required to pierce graft material 308 with needle 326, an RF electrode such as that described in FIG. 9 is used to form small opening 328.

FIG. 9 is a perspective view of an RF catheter 102A having an RF electrode 106A in accordance with another embodiment. Referring now to FIG. 9, RF catheter 102A includes an inner member 110A. Located at a distal end 110D of inner member 110A is RF electrode 106A. RF electrode 106A is electrically connected to an RF conductor 108A (indicated by the dashed lines) which extends along the length of inner member 110A.

RF electrode 106A is cone shaped, i.e., conical, in accordance with this example. More particularly, RF electrode 106A increases in diameter from a distal end 106D to a proximal end 106P of RF electrode 106A. Illustratively, the maximum outer diameter of RF electrode at proximal end 106P is 3 mm.

Inner member 110A is hollow and includes a guide wire lumen formed therein. As shown, a guide wire 120A exits inner member 110A at distal end 110D. RF electrode 106A has an opening formed through the center through which guide wire 120A passes. For example, RF electrode 106A sits on inner member 110A, which provides the dielectric between RF electrode 106A and guide wire 120A. These dielectrics can be comprised of temperature resistant plastics or ceramics.

RF catheter 102A further includes a delivery catheter 130A similar to delivery catheter 130 of FIG. 1 and so is not discussed again in detail.

Referring now to FIGS. 3 and 9 together, RF power is applied to RF electrode 106A to form an opening similar to small opening 328 in a graft material. In one example, the graft material is vaporized such that the opening is formed in the graft material without creation of a loose flap of graft material.

Figure 10:
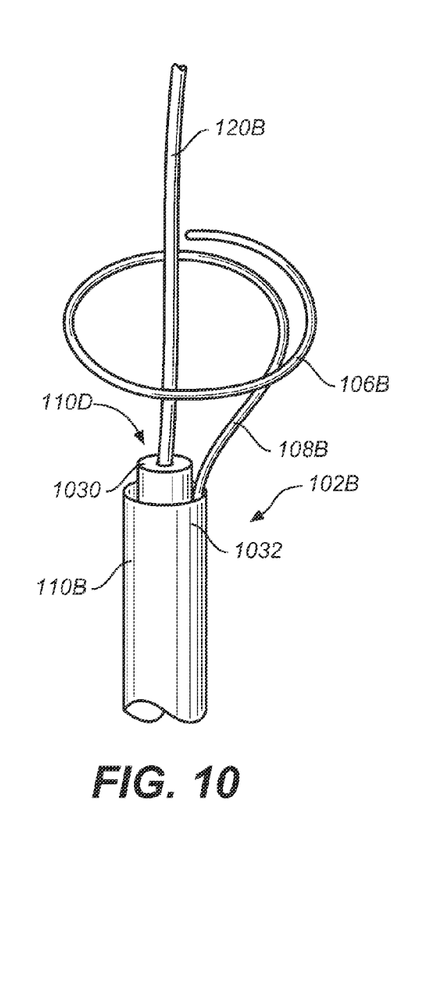
FIGS. 10, 11 and 12 are perspective views of RF catheters having RF electrodes in accordance with various embodiments.

FIG. 10 is a perspective view of an RF catheter 102B having an RF electrode 106B in accordance with another embodiment. Referring now to FIG. 10, RF catheter 102B includes an inner member 110B. In accordance with this example, inner member 110B is a coaxial structure including an inner tube 1030 and an outer tube 1032, e.g., shrink tubing. RF conductor 108B extends along the length of inner member 110B in the annular space between inner tube 1030 and outer tube 1032. RF electrode 106B is in a circular shape of an open circle, sometimes called a circular spiral, or a broken or non-continuous circle. Illustratively, RF conductor 108B and RF electrode 106B are parts of a single integral wire.

Inner member 110B is hollow and includes a guide wire lumen formed therein. As shown, a guide wire 120B exits inner member 110B at distal end 110D.

Figure 11:
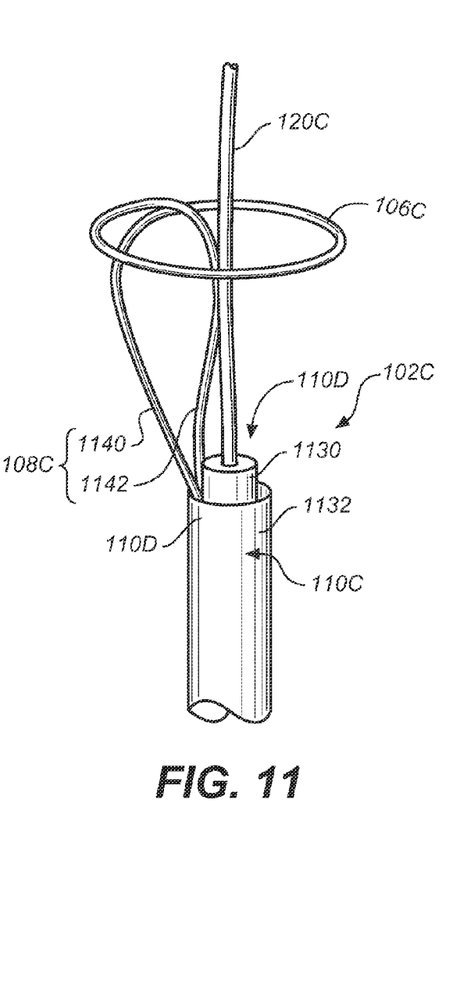

FIG. 11 is a perspective view of an RF catheter 102C having an RF electrode 106C in accordance with another embodiment. Referring now to FIG. 11, RF catheter 102C includes an inner member 110C. In accordance with this example, inner member 110C is a coaxial structure including an inner tube 1130 and an outer tube 1132, e.g., shrink tubing.

RF conductor 108C is formed by two side-by-side conductors 1140, 1142 extends along the length of inner member 110C in the annular space between inner tube 1130 and outer tube 1132. RF electrode 106C is in an open circular shape of an open circle. More particularly, RF electrode 106C is a circular spiral where the distal end of the circular spiral extends proximally back into inner member 11C. More particularly, conductors 1140, 1142, sometimes called a first conductor and a second conductor, both extend proximally from the open circular shape of RF electrode 106C at the same point along the circle. Illustratively, conductors 1140, 1142 and RF electrode 106C are parts of a single integral wire.

Inner member 11C is hollow and includes a guide wire lumen formed therein. As shown, a guide wire 120C exits inner member 110C at distal end 110D.

Figure 12:
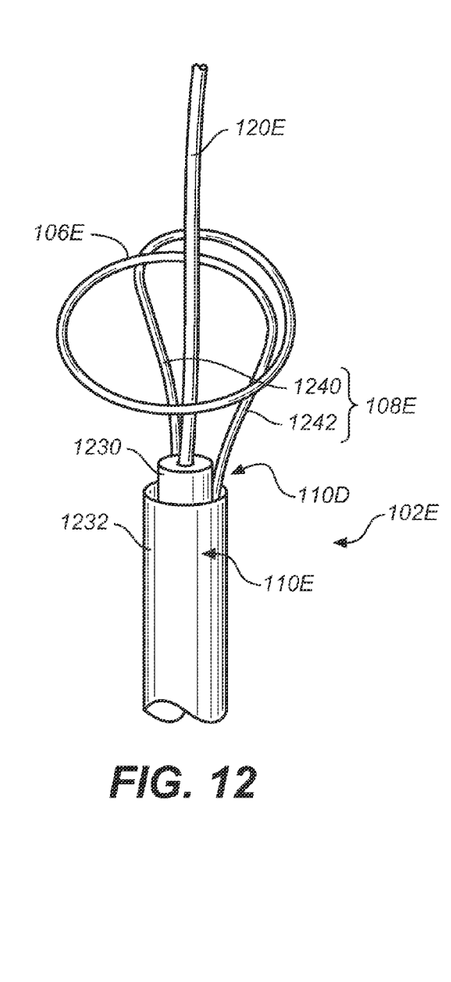

FIG. 12 is a perspective view of an RF electrode 102E having an RF electrode 106E in accordance with another embodiment. Referring now to FIG. 12, RF catheter 102E includes an inner member 110E. In accordance with this example, inner member 110E is a coaxial structure including an inner tube 1230 and an outer tube 1232, e.g., shrink tubing.

RF conductor 108E is formed by two side-by-side conductors 1240, 1242 extends along the length of inner member 110E in the annular space between inner tube 1230 and outer tube 1232.

RF electrode 106E is in an open circular shape. More particularly, RF electrode 106E is a circular spiral where the distal end of the circular spiral extends proximally back into inner member 110E. In accordance with this example, conductors 1240, 1242 both extend proximally from the open circular shape of RF electrode 106E at different point along the circle. Illustratively, conductors 1240, 1242 and RF electrode 106E are parts of a single integral wire.

Inner member 110E is hollow and includes a guide wire lumen formed therein. As shown, a guide wire 120E exits inner member 110E at distal end 110D.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A cutting radio frequency (RF) catheter assembly comprising:
    an inner member comprising a proximal end, a distal end, and a guide wire lumen extending from the proximal end to the distal end, wherein said inner member travels through a lumen when deploying said cutting RF catheter assembly to a location for cutting a prosthesis in the lumen;
    an RF electrode distal to the distal end of said inner member;
    a sheath radially constraining said RF electrode and enclosing the inner member,
    wherein said sheath travels through the lumen when deploying said cutting RF catheter assembly to said location for the cutting the prosthesis in the lumen; and
    wherein upon retraction of said sheath, said RF electrode is exposed and self expands into a circular shape;
    an RF conductor electrically connected to said RF electrode, and extending through said inner member and exiting the inner member at the distal end of the inner member;
    a guide wire in said guide wire lumen of said inner member and exiting the inner member at the distal end of the inner member when the RF conductor is extending through said inner member and exiting the inner member, wherein upon the expansion of the RF electrode into the circular shape, the guide wire is movable through, and movable distal to the circular shape of the RF electrode while the RF electrode is deployed; and
    a handle, said inner member being fixed relative to said handle, said sheath being movable relative to said handle.

2. The cutting RF catheter assembly of claim 1 wherein said RF conductor supports said RF electrode.

3. The cutting RF catheter assembly of claim 2 wherein said RF conductor comprises a dielectric material.

4. The cutting RF catheter assembly of claim 2 wherein said RF conductor and said RF electrode are parts of a single integral wire.

5. The cutting RF catheter assembly of claim 1 wherein said circular shape is a closed circle.

6. The cutting RF catheter assembly of claim 1 wherein said circular shape is an open circle.

7. The cutting RF catheter assembly of claim 6 wherein said RF conductor comprises a first conductor and a second conductor, said first conductor and said second conductor extending proximally from said open circle at a same point along said open circle.

8. The cutting RF catheter assembly of claim 6 wherein said RF conductor comprises a first conductor and a second conductor, said first conductor and said second conductor extending proximally from said open circle at different points along said open circle.

9. The cutting RF catheter assembly of claim 1 further comprising a delivery catheter comprising a lumen, said inner member and sheath being located in said lumen of said delivery catheter.

10. The cutting RF catheter assembly of claim 9 wherein said delivery catheter further comprises a radiopaque marker at a distal end of said delivery catheter.

11. The cutting RF catheter assembly of claim 1 further comprising an actuation button connected to a proximal end of said sheath, said actuation button extending through a slit of said handle.

12. The cutting RF catheter assembly of claim 1 further comprising an RF power supply electrically connected to said RF electrode.

13. The cutting RF catheter assembly of claim 12 further comprising a counter electrode electrically connected to said RF power supply.

14. The cutting RF catheter assembly of claim 1 wherein said guide wire comprises a dielectric material.

15. The cutting RF catheter assembly of claim 1 wherein said guide wire comprises a catching structure at a distal end of said guide wire.

16. A cutting radio frequency (RF) catheter assembly comprising:
    an inner member comprising a proximal end, a distal end, and a guide wire lumen extending from the proximal end to the distal end;
    an RF electrode distal to the distal end of said inner member, said RF electrode being a circular loop, wherein said inner member travels through a lumen when deploying said cutting RF catheter assembly to a location for cutting a prosthesis in the lumen;
    an RF conductor electrically connected to said RF electrode and extending through said inner member and exiting the inner member at the distal end of the inner member; and
    a guide wire in said guide wire lumen of said inner member and exiting the inner member at the distal end of the inner member when the RF conductor is extending through said inner member and exiting the inner member, wherein the guide wire is movable through and movable distal to the circular shape of the RF electrode while the RF electrode is deployed.

17. The cutting RF catheter assembly of claim 16 wherein said RF electrode comprises a super elastic memory material.

18. The cutting RF catheter assembly of claim 16 further comprising a sheath for delivering said RF electrode.

* * * * *